United States Patent [19]

Stanton et al.

[11] Patent Number: 4,776,974

[45] Date of Patent: Oct. 11, 1988

[54] STABLE ANTIMICROBIAL SANITIZING COMPOSITION CONCENTRATES CONTAINING ALKYL AMINE OXIDES

[75] Inventors: James H. Stanton; Lichorat James J.; John A. Lopes, all of Grosse Ile, Mich.

[73] Assignee: Diversey Wyandotte Corporation, Wyandotte, Mich.

[21] Appl. No.: 20,367

[22] Filed: Mar. 2, 1987

[51] Int. Cl.$^4$ .................................................. C11D 3/48
[52] U.S. Cl. ............................ 252/106; 252/174.19; 252/174.21; 252/554; 252/558; 252/DIG. 14; 252/547; 252/142; 422/28; 514/557; 514/558; 514/560
[58] Field of Search ............... 252/106, 174.19, 174.21, 252/DIG. 14, 550, 531, 554, 142, 542, 135, 558, 547; 422/28; 514/557, 558, 560

[56] References Cited

U.S. PATENT DOCUMENTS

| | | | |
|---|---|---|---|
| 3,150,096 | 9/1964 | Schmidt | 252/106 |
| 4,021,376 | 5/1977 | Lamberti et al. | 252/558 |
| 4,167,561 | 9/1979 | Lamberti et al. | 252/174.19 |
| 4,177,294 | 12/1979 | Lehmann et al. | 252/106 |
| 4,277,378 | 7/1981 | Asayii et al. | 252/546 |
| 4,382,871 | 5/1983 | Lamberti et al. | 252/174.19 |
| 4,404,040 | 9/1983 | Wang | 252/106 |
| 4,581,161 | 4/1986 | Nedonhelle | 252/174.19 |
| 4,715,980 | 12/1987 | Lopes et al. | 252/106 |

*Primary Examiner*—Josephine Barr
*Attorney, Agent, or Firm*—Arnold S. Weintraub

[57] ABSTRACT

Low-foaming antimicrobial concentrate and "use" composition comprising (a) an antimicrobial agent selected from the group consisting of monocarboxylic acids, dicarboxylic acids and mixtures thereof, (b) an alkyl N,N-dimethyl amine oxide solubilizer-coupling agent having between about 8 and about 10 carbon atoms in the alkyl portion, (c) an acid capable of yielding a pH less than or equal to about 5.0 upon dilution of the concentrate to a use solution, and (d) water. This composition provides effective storage stability and low-foaming sanitization when used in "in-place" processing lines such as dairies, breweries and other food processing facilities.

20 Claims, No Drawings

STABLE ANTIMICROBIAL SANITIZING COMPOSITION CONCENTRATES CONTAINING ALKYL AMINE OXIDES

BACKGROUND OF THE INVENTION

1. Cross-reference to Related Applications

This application is a continuation-in-part of U.S. Ser. No. 840,336, filed on Mar. 17, 1986, now U.S. Pat. No. 4,715,980 the disclosure of which is hereby incorporated by reference.

2. Field of the Invention

This invention relates to novel coupling agents which increase the stability of antimicrobial sanitizing and cleaning composition. This invention also relates to cleaning and sanitizing compositions which contain n-alkyl and/or n-alkenyl succinic acids as an active antimicrobial agent.

3. Background of the Prior Art

Various chemicals exhibit varying degrees of antimicrobial activity. Among these are short-chain monocarboxylic acids having less than twenty carbon atoms, quaternary ammonium compounds and hexachlorophene compounds. These compounds have been admixed with various surfactants and water to yield aqueous sanitizing solutions.

It has been found that the antimicrobial activity of these compounds can be increased when the sanitizer solution is acidified to a pH below about 5. Acid sanitizing solutions of this type are generally employed in food, beverage, brewery and other industries as a clean-in-place sanitizing solution for processing equipment.

Generally, antimicrobial solutions containing these antimicrobial agents are undesirable for use in food equipment cleaning applications. Residual amounts of the acid sanitizing solutions which remain in the equipment after cleaning can impart unpleasant tastes and odors to food. The cleaning solutions are difficult to rinse from the cleaned surfaces. Larger amounts of water are required to effectively completely remove conventional sanitizing solutions. Those sanitizers containing halogens can be corrosive to metal surfaces of food plants. Quaternary ammonium compounds strongly adhere to sanitized surfaces even after copious rinsing and may interfere with desired microbial growth during food processing; e.g. fermentation.

It has, also, been found that the antimicrobial activity of conventional acid sanitizing solutions can be adversely affected by the hardness of the water used in and with the solution. A marked decrease in antimicrobial activity has been noted at water hardness above about 500 ppm. Therefore, in order to assure sufficient antimicrobial activity, the hardness of water must be carefully adjusted to maintain the hardness below about 500 ppm.

The acid sanitizing solutions presently available are effective against gram negative and gram positive bacteria such as E. coli and Staph. aureus but are not as efficacious on any yeast contamination which can be present. In many applications control of yeast infestations requires a separate solution that that which is used to eliminate gram negative and gram positive bacteria. Use of two solutions can be costly and time consuming.

Such antimicrobial solutions are, generally, produced by admixture of water and an aqueous concentrate containing antimicrobial agents, water or other suitable diluents and acids capable of yielding a pH below about 5 upon dilutions. As can be appreciated, such antimicrobial concentrate compositions must exhibit homogeneity and solution stability during prolonged storage periods; particularly at low temperatures. To achieve this, solubilizers or coupling agents are added to the concentrate to maintain stability of the solution at high acid concentrations at prolonged low temperatures or during repeated freeze/thaw cycles.

Such solubilizers are, generally, surfactant hydrotropes capable of solubilizing the antimicrobial agent in the acidic concentrate while maintaining it in active form in both the concentrate and in the diluted antimicrobial solution suitable for conventional use. Various anionic, zwitterionic and nonionic surfactants or mixtures thereof have been previously employed in such solutions.

These solubilizers, when used in antimicrobial compositions, tend to cause undesirable foaming, thus requiring the addition of foam suppressants. Additionally, these solubilizers did not provide stability of the antimicrobial concentrate compositions over a wide range of storage temperatures.

Thus, it is desirable to provide a stable antimicrobial concentrate which can provide an antimicrobial solution which is equally effective on gram negative and gram positive bacteria and on yeast. It is desirable that the antimicrobial activity of the solution be unaffected by water hardness. It is also desirable that the composition provide a low-foaming antimicrobial use solution.

SUMMARY OF THE INVENTION

In accordance herewith, there is provided an antimicrobial sanitizing composition concentration which is capable of being diluted with a major amount of a food grade diluent to form an antimicrobial use solution. The concentrate composition hereof, generally, comprises:

(a) an antimicrobial agent selected from the group consisting of a monocarboxylic acid, a dicarboxylic acid and mixtures thereof wherein the monocarboxylic acid has the general formula:

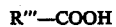

wherein R''' is a straight chain or branched, saturated or unsaturated alkyl radical having between about 6 and about 12 carbon atoms, and the dicarboxylic acid has the general formula:

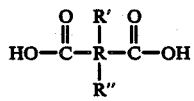

wherein R is a saturated or unsaturated hydrocarbon moiety having two carbon atoms; R' is a substituted or unsubstituted n-alkyl or n-alkenyl moiety having between about 6 and about 12 carbon atoms; and R'' is a functional group selected from the group consisting of hydrogen and alcohols: Where R' is substituted, suitable substituents including thiols, methane thiols, amines, methoxy compounds and various aromatic compounds;

(b) an alkyl N,N-dimethyl amine oxide solubilizer having between about 8 and about 10 carbon atoms in the alkyl portion;

(c) an anionic diluent; and (d) an acid capable of yielding a solution pH less than or equal to about 5.0 upon dilution of the concentrate to a use solution.

The present invention, also, provides an antimicrobial "use solution" which is particularly suited for "in place" cleaning. The use solution comprises:

(a) between about 10 parts per million (ppm) to about 500 ppm of the defined antimicrobial agent;
(b) at least about 10 ppm of the defined solubilizer-coupling agent;
(c) the anionic diluent;
(d) the acid sufficient to yield a pH less than or equal to 5; and
(e) water.

The present invention further contemplates a method of using the dilute composition in cleaning "in place" systems, such as are found in dairies and breweries. The method hereof involves the circulation of the sanitizing solution through the system at ambient temperatures followed by an optional rinse phase with potable water.

The type and amount of the above-listed components can be varied so that compositions the effectiveness and characteristics desired.

For a more complete understanding of the present invention, reference is made to the following detailed description and accompanying examples.

DETAILED DESCRIPTION OF THE PREFERRED EMBODIMENT

The antimicrobial sanitizing composition of the present invention is predicted on the unexpected discovery that certain monocarboxylic and dicarboxylic acids or mixtures thereof exhibit enhanced antimicrobial activity, at pH levels at or below about 5.0.

The antimicrobial sanitizing composition of the present invention is further predicated on the discovery that certain alkyl derivatives of amine oxides provide enhanced solubilizing action in concentrated acidic solutions containing antimicrobial agents such as monocarboxylic acids and dicarboxylic acids, without increasing the foaming action of diluted use solutions made therefrom. It has also been found that these substituted amine compounds enhance the low- and high-temperature stability of antimicrobial concentrates in which they are employed.

The term "sanitizing" as used herein to indicate reduction of undesirable microorganisms by about five orders of magnitude or greater within time periods set forth below.

The antimicrobial sanitizing composition concentrate of the present invention, as noted, generally, comprises:

(a) an antimicrobial agent selected from the group consisting of a monocarboxylic acid, a dicarboxylic acid and mixtures thereof, the monocarboxylic acids having the general formula:

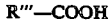

wherein R''' is a straight or branched, saturated or unsaturated alkyl radical having between about 6 and about 12 carbon atoms; the dicarboxylic acid having the general formula:

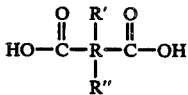

wherein R is a saturated or unsaturated hydrocarbon moiety having two carbon atoms; R' is selected from the group consisting of substituted or unsubstituted n-alkyl and n-alkenyl radicals having 6 to 12 carbon atoms; suitable substituents for R' including thiols, methane thiols, amines, methoxy compounds, aryls and mixtures thereof, and R'' may be hydrogen or an alcohol;

(b) an alkyl N,N-dimethyl amine oxide solubilizing agent having between about 8 and 10 carbon atoms in the alkyl portion;
(c) an anionic diluent; and
(d) an acid present in an amount sufficient to yield a use solution having a pH at or below 5.0.

The concentrate, generally, comprises:

(a) from about 0.25 to about 25 percent, by weight, of the defined antimicrobial agent, based on the total weight of the concentrate;
(b) from about 0.25 to about 20.0 percent, by weight, based on the total weight of the concentrate, of the defined solubilizer-coupling agent;
(c) from about 10.0 to about 95.5 percent, by weight, based on the total weight of the concentration, of the diluent; and
(d) from about 4.0 to about 50.0 percent, by weight, based on the total weight of the concentrate, of the defined acid.

The concentrate as well as the use solution made therefrom can incorporate other conventional antimicrobial agents such as quaternary ammonium compounds etc. Also, various dyes, perfumes, etc. can be employed either in the concentrate or the use solution.

The antimicrobial sanitizing composition of the present invention in its concentrated form can be effectively diluted with water or another suitable diluent such as various short-chain alcohols to provide a use solution having between about 10 ppm and about 500 ppm of the carboxylic acid antimicrobial agent while maintaining the pH at or below 5.0 without compromising the effectiveness of the solution.

In practicing the present invention, and as noted hereinabove, the antimicrobial agent may be either a mono- or dicarboxylic acid. Preferably, the dicarboxylic acid is employed.

The preferred dicarboxylic acids employed in the present invention are those having a four-carbon saturated or unsaturated backbone.

Without being bound to any theory, the unexpected efficacy of the dicarboxylic acid moiety over monocarboxylic equivalents appears to be related to the lower vapor pressures of the dicarboxylic acid moieties. The lower vapor pressures aid in keeping the resulting sanitizers use solution free from undesirable organoleptic properties associated with organic acids. Furthermore, it appears that straight-chain unsaturation increases the solubility of the material in an aqueous environment without adversely affecting antimicrobial properties.

Specifically, the dicarboxylic acids employed herein are selected from the group consisting of succinic acid, maleic acid and fumaric acid and, preferably, succinic acid. The preferred succinic acids employed in the present invention are selected from the group consisting of n-octyl succinic acid, n-octenyl succinic acid, n-nonyl succinic acid, n-nonenyl succinic acid, n-decyl succinic acid, n-decenyl succinic acid, n-hexyl succinic acid, n-hexenyl succinic acid, diisobutenyl succinic acid, methyl heptenyl succinic acid and mixtures thereof.

It has also been found that admixture of dicarboxylic acids with certain short-chain monocarboxylic acids can also be efficacious in antimicrobial compositions of this type. Preferred monocarboxylic acids are selected from the group consisting of capric acid, caprylic acid, neodecanoic acid, decanoic acid, octanoic acid, 2,2 dimethyl octanoic acid and mixtures thereof.

It is to be understood however, and it is also within the purview of this invention to employ monocarboxylic acids independently as the antimicrobial agent in admixture with the solubilizer-coupling agent of the present invention.

The alkyl N,N-dimethyl amine oxide solubilizing agent employed herein is a compound capable of solubilizing the antimicrobial agent in an acidic diluent while maintaining the agent in active form in both the concentrate and the diluted use solution of the product under use conditions. Various alkyl N,N-dimethyl amine oxides can be successfully employed in this invention. These compounds have been found to have greater solubilizing ability than conventional solubilizing agents. Additionally, the alkyl N,N-dimethyl amine oxides solubilizing agents have been found to be low-foaming when used in antimicrobial use solutions such as those of the present invention. Additionally, such compositions remain clear and stable over a broad range of temperatures from about $-10°$ F. to about $120°$ F.

The alkyl N,N-dimethyl amine oxide solubilizing agents useful herein have between 8 and 10 carbon atoms in the alkyl portion. These compounds are, respectively, octamine, N,N-dimethyl-, N-oxide and 1-decanamine, N,N-dimethyl-, N-oxide. The preferred amine oxide is octanamine, N,N-dimethyl, N-oxide because of its lower foam characteristics. The amine oxides contemplated for use herein are commercially available from Sherex Corporation as a 47.4 percent amine oxide solution solid under the trade names Sherex EPSC 192-65 and EPSC 192-64, respectively. These materials provide antimicrobial sanitizer compositions with low foaming action and good broad range temperature stability. Furthermore, the material can be used as a total substitute for anionic, nonionic or zwitterionic surfactants previously employed in antimicrobial sanitizers of this type; thus eliminating unpleasant odors associated with the use of such conventional surfactants.

The anionic diluent employed is, preferably, potable drinking water. However, other compatible diluents such as C-1 to C-3 short-chain alcohols, may be employed.

An noted hereinabove, the antimicrobial sanitizing concentrate of the present invention also contains an acid capable of providing a solution pH at or below about 5.0 when the concentrate is diluted to its use solution strength. The acid employed must be compatible with the other components of the antimicrobial sanitizing solution, i.e., it must not produce instability or cause degradation or deactivation of the surfactant or dicarboxylic acid. The acid can be either a weak organic acid such as acetic acid, hydroxyacetic acid, citric acid, tartaric acid, maleic acid, fumaric acid or mixtures thereof or an inorganic acid such as phosphoric acid, sulfuric acid, sulfamic acid or mixtures thereof. Preferably, phosphoric acid is employed.

The concentrate hereof is, generally, prepared by mixing the components together at ambient conditions, with heating, if necessary.

The concentrate hereof, as noted, is capable of forming a use solution when the concentrate is admixed with an anionic diluent such as water. The use solution thus formed generally comprises:

(a) from about 10 parts per million (ppm) to about 500 ppm of the defined antimicrobial agent;
(b) from about 10 ppm to about 500 ppm of the defined solubilizer-coupling agent.
(c) the anionic diluent originally present in the concentrate;
(d) quantities of the organic or inorganic acid noted above sufficient to yield a use solution pH below about 5.0; and
(e) water as the balance of the composition.

The antimicrobial sanitizing composition of the present invention may be successfully employed in sanitizing and disinfecting fixed-in-place food processing facilities such as those found in dairies, breweries and beverage plants. The composition of the present invention exhibits antimicrobial activity at ambient temperature.

To sanitize, the diluted use solution is circulated through the system for an interval sufficient to contact and kill undesirable microorganisms. This can be anywhere from less than about 30 seconds to about 10 minutes depending on the type and amount of contamination present. Ordinarily, the contact-time will be in the range of about one minute to about two minutes. After sanitizing, the sanitizing composition is drained from the system.

In most cleaned-in-place applications, the system can be brought back into service immediately after the sanitizing solution is removed. However, the system may be rinsed with potable water or any other suitable material after sanitizing.

For a more complete understanding of the present invention, reference is made to the following examples. The examples are to be construed as illustrative and not limitative of the present invention.

EXAMPLE I

Decyl succinic acid was prepared from decyl succinic anhydride by thermal hydrolysis. Two solutions of decyl succinic acid were prepared. A quantity of 75 percent phosphoric acid was added to one of the decyl succinic acid solutions such that the resulting solution contained 1 percent decyl succinic acid and 15 percent phosphoric acid. The remaining decyl succinic acid solution contained 1 percent succinic acid with no additives.

A one-part sample of the acidified decyl succinic acid solution was admixed with 100 parts of water having 500 ppm synthetic water hardness present as calcium carbonate to yield a solution containing 100 ppm decyl succinic acid. The resulting sanitizing solution was exposed to challenge bacteria *Staphylococcus aureus* ATCC 6538 and *Escherichia coli* ATCC 11229 to determine antimicrobial effectiveness. The test procedure employed was the Germicidal and Detergent Sanitizer Test recommended by the Association of Official Analytical Chemists. The test was carried out at 77° F. and the results are found in Table I.

A 50 ppm sample and a 25 ppm sample of the diluted acidified decyl succinic acid solution were prepared by admixing 0.5 part and 0.25 part samples of acidified 1 percent decyl succinic acid solutions, respectively, with 100 parts water containing 500 ppm hardness present as calcium carbonate ($CaCO_3$). The samples were exposed to the challenge bacteria *E. coli* and *Staph. aureus*, according to the A.O.A.C. test procedures outlined above. The results are found in Table I.

A sample containing 100 ppm of the non-acidified decyl succinic acid sample was also prepared using water having 500 ppm hardness and was exposed to the challenge bacteria. The resulting data is also found in Table I.

As can be seen from the data in Table I, the decyl succinic acid solution exhibited bacteriocidal activity under acidic conditions.

TABLE I

Evaluation of Antimicrobial Activity of Decyl Succinic Acid

| Formulation (% by weights) | Dilution (mls of Formulation per 100 ml water) | Amount of Succinic Acid Derivative (ppm) | Percent Kill at given intervals | | | |
|---|---|---|---|---|---|---|
| | | | Staph. aureus | | E. coli | |
| | | | 30 sec. | 60 sec. | 30 sec. | 60 sec. |
| a. 1 percent decyl succinic acid in water | 1.0 | 100 | <99.99 | <99.99 | <99.99 | <99.99 |
| b. 1 percent decyl succinic acid with 15 percent phosphoric acid in water | 1.0 | 100 | ≧99.999 | ≧99.999 | ≧99.999 | ≧99.999 |
| | 0.5 | 50 | ≧99.999 | ≧99.999 | ≧99.999 | ≧99.999 |
| | 0.25 | 25 | ≧99.999 | ≧99.999 | ≧99.999 | ≧99.999 |

EXAMPLE II

The antimicrobial activity of n-octyl, n-octenyl and n-decenyl succinic acids were evaluated according to the procedure discussed in Example I using *Staph. aureus* as the challenge bacteria. The resulting data are found in Table II.

As can be seen from the data in Table II, n-octyl, n-octenyl and n-decenyl succinic acids exhibit microbicidal activity in the presence of acidic solutions in concentrations at or above 100 ppm dicarboxylic acid even in water having a hardness of 500 ppm present as calcium carbonate.

TABLE II

Evaluation of Antimicrobial Activity of Decyl Succinic Acid

| Formulation (% by weights) | Dilution (mls of Formulation per 100 ml water) | Amount of Succinic Acid Derivative (ppm) | Percent kill, Staph. aureus Staph. Aureus | |
|---|---|---|---|---|
| | | | 30 sec. | 60 sec. |
| a. 5.0 percent n-octenyl n-succinic acid 10.0 percent sodium xylene sulfonate, 40.0 percent phosphoric acid and 45 percent water | 0.4 | 200 | ≧99.999 | ≧99.999 |
| | 0.25 | 100 | ≧99.999 | ≧99.999 |
| | 0.1 | 50 | ≧99.99 | ≧99.99 |
| b. 5.0 percent n-octyl succinic acid, 10.0 percent sodium xylene sulfonate, 40.0 percent phosphoric acid and 45 percent water | 0.4 | 200 | ≧99.999 | ≧99.999 |
| | 0.25 | 100 | ≧99.999 | ≧99.999 |
| | 0.1 | 50 | ≧99.99 | ≧99.99 |
| c. 5.0 percent n-decyl succinic acid, 8.0 percent sodium xylene sulfonate, 50.0 percent phosphoric acid and 37 percent water | 0.4 | 300 | ≧99.999 | ≧99.999 |
| | 0.2 | 100 | ≧99.999 | ≧99.99 | a. water containing 500 ppm synthetic hardness (as Calcium Carbonate)

EXAMPLE III

A antimicrobial sanitizing composition containing n-octenyl succinic acid, sodium xylene sulfonate (a surfactant hydrotrope), phosphoric acid and water was tested according to the guidelines discussed in Example I. The challenge yeast *Candida albicans* ATCC 14053 was employed. The *C. albicans* used was grown on Saboraud's agar for 24 hours at 30° F. on a rotary shaker to ensure a sufficient number of challenge organisms. The resulting data are found in Table III.

As is shown by the data found in Table III, an antimicrobial acid sanitizing solution containing a succinic acid derivative exhibits yeasticidal activity.

TABLE III

Evaluation of Yeasticidal Activity of n-Octenyl Succinic Acid

| Formulation, by weight | Mls of Formulation per 100 ml water[a] | Amount of Succinic Acid Derivative (ppm) | Percent kill of C. Albicans Detected at Given Intervals | | |
|---|---|---|---|---|---|
| | | | 5 min. | 10 min. | 15 min. |
| 5 percent n-octenyl succinic acid; 40 percent phosphoric acid; and 10 percent xylene sulfonate 45 percent water | 0.4 | 200 | <99.99 | <99.99 | <99.99 |
| | 0.8 | 400 | ≧99.999 | ≧99.999 | ≧99.999 |

[a]Water containing 500 ppm synthetic hardness as calcium carbonate.

EXAMPLE IV

Antimicrobial sanitizing use solutions were prepared. Each solution contained 500 ppm sodium xylene sulfonate, 0.15 percent phosphoric acid and 500 ppm of one of the dicarboxylic acids listed in Table IV. The balance of each use solution was water.

Each solution was tested against challenge bacteria *E. coil* and *Staph. aureus* according to the procedure outlined in Example I to determine bacteriocidal activity. The results are found in Table IV.

As is shown by the data found in Table IV, dicarboxylic acid derivatives of various n-alkyl, n-alkenyl or branched carbon chain groups show bacteriocidal activities under acidic conditions.

TABLE IV

Evaluation of Bacteriocidal Activity of Various n-Alkyl, n-Alkenyl or Branched Succinic Acids Under Acidic Conditions

| | | Percent Kill | | | |
|---|---|---|---|---|---|
| | | Staph. aureus | | E. coli | |
| Compound | PPM | 30 Sec | 60 Sec | 30 Sec | 60 Sec |
| n-Hexyl Succinic Acid | 500 | ≧99.999 | ≧99.999 | ≧99.999 | ≧99.999 |
| n-Decyl Succinic Acid | 500 | ≧99.999 | ≧99.999 | <99.99 | <99.99 |
| n-Dodecyl Succinic Acid | 500 | ≧99.999 | ≧99.999 | <99.99 | <99.99 |
| n-Hexenyl Succinic Acid | 500 | <99.99 | ≧99.999 | <99.99 | <99.99 |
| n-dodecenyl Succinic Acid | 500 | ≧99.999 | ≧99.999 | <99.99 | <99.99 |
| Diisobutenyl Succinic Acid | 300 | ≧99.999 | ≧99.999 | ≧99.999 | ≧99.999 |
| Methyl Heptenyl Succinic Acid | 300 | >99.999 | ≧99.999 | ≧99.999 | ≧99.999 |
| Nonenyl Succinic Acid | 300 | ≧99.999 | ≧99.999 | ≧99.999 | ≧99.999 |

Each test solution contained an amount of sodium xylene sulfonate equal to that of the dicarboxylic acid derivative and 0.15 percent, by weight, phosphoric acid.

TABLE V

Evaluation of Yeasticidal Activity of Various Succinic Acids Under Acidic Conditions

| | | Percent Kill *Saccharomyces cerevisiae* Detected at given intervals | |
|---|---|---|---|
| Compound | PPM | 5 Min | 10 Min |
| n-Octenyl Succinic Acid | 600 | ≧99.999 | ≧99.999 |
| | 800 | ≧99.99 | ≧99.999 |
| n-Decenyl Succinic Acid | 300 | ≧99.999 | ≧99.999 |
| | 600 | ≧99.999 | ≧99.999 |
| n-Octyl Succinic Acid | 300 | <99.99 | ≧99.99 |
| | 600 | ≧99.999 | ≧99.999 |
| Methyl Heptenyl Succinic Acid | 600 | <99.99 | ≧99.999 |
| | 800 | ≧99.999 | ≧99.999 |

Each test solution contained an amount of sodium xylene sulfonate equal to that of the dicarboxylic acid derivative and 0.15 percent, by weight, of phosphoric acid.

EXAMPLE V

Various antimicrobial sanitizing use solutions were prepared. Each solution contained 0.15 percent phosphoric acid and equal parts sodium xylene sulfonate and one of the dicarboxylic acids listed in Table V. The balance of each use solution was water.

The challenge yeast *Saccharomyces cerevisiae* ATCC 7754 was grown on Saboraud's agar for 48 hours at 30° C. Cell suspensions made from this growth were tested against the use solutions listed in Table V according to the guidelines discussed in Example I. The results are found in Table V.

As is shown by the data found in Table V, the dicarboxylic acid derivatives of various n-alkyl and n-alkenyl groups show yeasticidal activities under acidic conditions.

EXAMPLE VI

Five different antimicrobial sanitizer use solution compositions each containing 500 ppm n-octenyl succinic acid, 500 ppm sodium xylene sulfate and sufficient amounts of disodium hydrogen phosphate and citric acid to give the five sanitizer compositions a pH of 3.0, 3.4, 3.9, 4.4 and 4.9, respectively. Each composition was tested according to the procedure discussed in Example I using *Staph. aureus* and *E. coli* as the challenge bacteria.

As shown by the data in Table VI, antimicrobial compositions containing n-octenyl succinic acid are efficacious in killing challenge bacteria at pH levels below about 5.0.

TABLE VI

Evaluation of Bacteriocidal Activity of n-Octenyl Succinic Acid at Various pH Levels

| Compound, ppm | | Citrate | Percent Kill | | | |
|---|---|---|---|---|---|---|
| n-Octenyl Succinic Acid | Sodium Xylene Sulfonate | Phosphate Buffer, pH | Staph. aureus | | E. coli | |
| | | | 30 Sec | 60 Sec | 30 Sec | 60 Sec |
| 500 | 500 | 3.0 | ≧99.999 | ≧99.999 | ≧99.999 | ≧99.999 |
| 500 | 500 | 3.4 | ≧99.999 | ≧99.999 | ≧99.999 | ≧99.999 |
| 500 | 500 | 3.9 | ≧99.999 | ≧99.999 | ≧99.999 | ≧99.999 |
| 500 | 500 | 4.4 | ≧99.999 | ≧99.999 | ≧99.99 | ≧99.999 |
| 500 | 500 | 4.9 | <99.99 | <99.99 | <99.99 | <99.99 |

EXAMPLE VII

A concentrated antimicrobial solution was prepared according to the present invention. N-octenyl succinic acid was prepared by the thermal hydrolysis of 1394 grams of n-octenyl succinic anhydride with 200 grams of water. Seven hundred and ninety-five grams of n-octenyl succinic acid was admixed with 757 grams of sodium xylene sulfonate and 3652 grams of tap water. The resulting solution was then acidified with 4258 grams of 75 percent phosphoric acid. The resulting composition is designated Composition A and is set forth in Table VII.

In order to make a use solution from the sanitizing concentrate which contains 200 ppm of n-octenyl succinic acid, 0.195 ml of the formulation Composition A (specific gravity 1.24) was admixed with 100 ml of water having a synthetic hardness of 500 ppm expressed as calcium carbonate. The resulting solution had a pH of 2.54.

A second composition was made in which the n-octenyl succinic acid was omitted. This composition is designated Composition B and is also set forth in Table VII.

A third composition was made in which an equal amount of n-decenyl succinic acid was substituted for the n-octenyl succinic acid. The resulting composition is set forth in Table VII as Composition C.

A fourth composition was prepared containing linear alkyl benzene sulfonate, phosphoric acid and water. The resulting composition is designated as Composition D and is set forth in Table VII.

The composition A, B and C were diluted with water containing 500 ppm synthetic hardness in the amounts shown in Table VIII and IX. These samples were tested according to the method disclosed in Example I using the challenge bacteria *Staph. aureus* and *E. coli*. The results are presented in Table VIII. The diluted samples in compositions A, B and C were tested according to the procedure outlined in Example VI using the challenge yeasts *Candida albicans* and *Saccharomyces cerevisiae*. The results are found in Table IV.

Diluted sanitizer concentrates containing dicarboxylic acids and prepared according to the present invention are more effective against *Staph. aureus* and *E. coli* than those solutions in which the dicarboxylic acid is omitted as is indicated by the data in Table VIII.

As shown from the data in Table IX diluted sanitizer concentrates containing dicarboxylic acids exhibit yeasticidal activity far greater than those that do not contain dicarboxylic acids.

TABLE VII

| Compound | Amount (% by Weight) |
|---|---|
| COMPOSITION A: | |
| n-Octenyl Succinic Acid | 8.0 |
| Sodium Xylene Sulfonate | 8.0 |
| 75% Phosphoric Acid | 45.0 |
| Tap Water | 39.0 |
| COMPOSITION B: | |
| Sodium Xylene Sulfonate | 8.0 |
| 75% Phosphoric Acid | 45.0 |
| Tap Water | 47.0 |
| COMPOSITION C: | |
| n-Decenyl Succinic Acid | 8.0 |
| Sodium Xylene Sulfonate | 8.0 |
| 75% Phosphoric Acid | 45.0 |
| Tap Water | 39.0 |
| COMPOSITION D: | |
| Linear Alkyl Benzene Sulfonate | 2.5 |
| 75% Phosphoric Acid | 20.0 |
| Tap Water | 77.5 |

TABLE VIII

Comparison of Bacteriocidal Activity of Compositions A, B and C

| | Use Concentrations mls/100 ml | Percent Kill | | | |
|---|---|---|---|---|---|
| | | Staph. aureus | | E. coli | |
| | | 30 Sec | 60 Sec | 30 Sec | 60 Sec |
| Composition A (from Table VII) | 0.2 | >99.999 | >99.999 | >99.999 | >99.999 |
| Composition B (from Table VII) | 0.8 | <99.99 | <99.99 | <99.99 | <99.99 |
| Composition C (from Table VII) | 0.2 0.3 0.4 | | | | |

TABLE IX

Comparison of Yeasticidal Activity of Compositions A, B and C

| | Use Concentration mls/100 ml | Percent Kill Candida albicans | | | |
|---|---|---|---|---|---|
| | | 5 min | 10 min | 15 min | 20 min |
| Composition A (from Table VI) | 0.4 | <99.99 | <99.99 | <99.99 | <99.99 |
| | 0.6 | ≧99.999 | ≧99.999 | ≧99.999 | ≧99.999 |
| Composition B (from Table VII) | 0.8 | <99.99 | <99.99 | <99.99 | <99.99 |
| Composition C (from Table VII) | 0.1 | ≧99.999 | ≧99.999 | ≧99.999 | ≧99.999 |
| | 0.2 | ≧99.999 | ≧99.999 | ≧99.999 | ≧99.999 |

EXAMPLE VIII

The foaming properties of compositions prepared according to the present invention were evaluated. Compositions A, C and D listed in Table VII were compared. Use solutions of Compositions A, C and D were prepared by diluting a portion of the respective composition with water containing 500 ppm synthetic hardness present as calcium carbonate. The dilution standards are set forth in Table X.

Five Hundred milliliter samples of each of the diluted Compositions A, C and D were each placed in a transparent cylinder. Each solution was circulated at a rate of 2 liters per minute for three minutes at 25° C. and was allowed to fall back into the cylinder on a baffle to generate foam. After three minutes, the circulation was stopped and the foam height recorded. The results are presented in Table X.

It was found that Composition A showed minimal foaming activity even when tested at a concentration four times above the conventional use levels of 200 ppm. However, Composition C which contained a different dicarboxylic acid showed high levels of foam comparable to Composition D, a known high-foaming composition. Thus, the microbial sanitizing compositions of the present invention can be either high-foaming or low-foaming depending on the choice of dicarboxylic acid.

TABLE X

Forming Ability of Compositions A, B and C

| | Dilution (%) v/v | Dicarboxylic Acid (ppm) | Foam Height (cm) After Given Intervals | |
|---|---|---|---|---|
| | | | 15 sec | 30 sec |
| Composition A (from Table VII) | .195 | 200 | 0.0 | 0.0 |
| | .585 | 600 | 0.0 | 0.0 |
| | .78 | 800 | 1.5 | 1.0 |
| Composition C (from Table VII) | .195 | 200 | 46.0 | 28.0 |
| Composition D (from Table VII) | .78 | a | 41.0 | 38.0 | a. Contains 200 ppm linear alkyl benzene sulfonate rather than dicarboxylic acid.

EXAMPLE IX

Minimum inhibitory concentrations (mic) of n-alkenyl succinic acid derivatives effective against gram positive microorganisms were determined using differing concentrations of n-octenyl succinic acid and n-decenyl succinic acid in 10 ml of nutrient broth for tests against *Staph. aureus* and Saboraud's broth for tests against *Saccharomyces cerevisiae*. These concentrations of succinic acid derivatives were inoculated with 0.1 ml of a 1 to 100 dilution of the challenge cultures. The challenged concentrations were incubated for 24 hours at 37° C. in the case of *Staph. aureus* and 30° C. in the case of *Saccharomyces cerevisiae*. Presence or absence of growth was recorded.

The results collected in Table XI indicate that N-octenyl succinic acid has a minimum inhibitory concentration of 1000 ppm against *Staph. aureus*. N-decenyl succinic acid showed a minimum inhibitory concentration of 1000 against *Staph. aureus* and 500 ppm against *Saccharomyces cerevisiae*.

TABLE XI

Inhibition of Gram Positive Microorganisms by Succinic Acid Derivatives at Various Concentrations

| | 50 ppm | 100 ppm | 250 ppm | 500 ppm | 1000 ppm |
|---|---|---|---|---|---|
| | n-Decenyl succinic acid | | | | |
| *Staph. aureus* | + | + | + | + | − |
| *Saccharomyces cerevisiae* | + | + | + | − | − |
| | n-Octenyl succinic acid | | | | |
| *Staph. aureus* | + | + | + | + | − |
| *Saccharomyces cerevisiae* | + | + | + | + | + |

+ indicates growth
− indicates no growth

EXAMPLE X

In order to determine the effectiveness and stability of antimicrobial concentrate compositions containing conventional solubilizer-coupling agents, two compositions were paired, the formulae of which are set forth in Table XII and designated as Compositions E and F.

Use solutions made from Compositions E and F were prepared in which the ratio of concentrate composition was 1 oz. concentrate to 4 gallons water and 1 oz. concentrate to 6 gallons water, respectively. Both use solutions exhibited antimicrobial activity.

A sample of Composition E, the 4x sample, was then tested at a variety of temperatures to determine its low-temperature stability. The composition became unhomogenous at 40° F. Because of this, the more concentrated composition, Composition F, was not tested.

A sample of Composition E was also frozen to determine the effects of a freeze/thaw cycle on this material. The material was unstable during freeze/thaw. Because of this, the more concentrated sample was not tested.

As can be observed from these test, antimicrobial concentrates containing sodium xylene sulfonates have certain instability problems which can hamper their general usefulness.

TABLE XII

| Materials | Composition E (wt. %) | Composition F (wt. %) |
|---|---|---|
| OSA[1] | 8 | 9.1 |
| SXS, 95%[2] | 8 | 15.0 |
| Phosphoric Acid, 75% | 45 | 40.0 |
| Water | 39 | 27.8 |
| C-8, C-10 fatty acid | — | 8.0 |

[1]octenyl succinic acid
[2]sodium xylene sulfonate

EXAMPLE XI

A variety of antimicrobial concentrate compositions were prepared employing n-octenyl succinic acid in combination with either sodium xylene sulfonate, sodium 1-octane sulfonate or octanamine, N,N-dimethyl-N-oxide (ODI) as the solubilizer coupling agent. The amounts of solubilizer-coupling agent listed in Table XIII are the minimum amounts necessary to obtain stable concentrates at room temperature. Each sample was, then, checked for stability by storing at 120° F. 40° F. and −10° F. As can be seen from the results set forth in Table XIII, stability was achieved with lower levels of ODI. Additionally, the samples containing ODI were the only samples stable over these temperature ranges.

Foam levels are use concentrations of 0.2 percent were compared using two foam tests, the results of which are summarized in Table XIII. In the first foam test, 100 ml of each 0.2 percent use solution were placed in a 250 ml. of graduated cylinder. The cylinder was then inverted 10 times. Foam levels were measured immediately after the inversions and again after a 30 second interval had elapsed. The foam heights are recorded in Table XIII. As can be seen from the data collected therein, ODI exhibited the lowest foaming characteristics.

Foam results were also compared with the dynamic foam tester. In this method a small pump having a capacity of 2,600 ml/min. is used to pump solution out of a plastic chamber having a three-inch diameter, through a one-quarter inch orifice and back into the three-inch diameter chamber. Foam height is measured after 30 seconds of circulation. The results are shown in Table XIII. As can be seen from this data, ODI exhibited foaming tendencies equal to those with sodium xylene sulfonate.

TABLE XIII
COMPARISON OF STABILITY AND FOAMING CHARACTERISTICS OF VARIOUS ANTIMICROBIAL COMPOSITIONS

| Concentrate Formulation | G wt % | H wt % | I wt % | J wt % | K wt % | L wt % |
|---|---|---|---|---|---|---|
| Sanitizing Agent: | | | | | | |
| n-octenyl succinic acid | 9.0 | 9.0 | 9.0 | 9.0 | 9.0 | 9.0 |
| capric-caprylic acid | | | | 2.0 | 2.0 | 2.0 |
| Solubilizer-Coupling Agent: | | | | | | |
| sodium xylene sulfonate (40%) | 25.0 | | | 30.0 | | |
| sodium 1-octane sulfonate (40%) | | 36.0 | | | 38.0 | |
| octanamine, N,N,—dimethyl N—oxide (47%) (ODI) | | | 18.0 | | | 17.0 |
| Phosphoric Acid (75%) | 55.0 | 55.0 | 55.0 | 50.0 | 50.0 | 50.0 |
| Water | 11.0 | — | 18.0 | 9.0 | — | 22.0 |
| Stability: | | | | | | |
| at RT | $C^1$ | $C^1$ | $C^1$ | $C^1$ | $C^1$ | $C^1$ |
| 120° F. | $St^2$ | $St^2$ | $St^2$ | $St^2$ | $St^2$ | $St^2$ |
| 40° F. | St | Sep | St | St | Sep | St |
| −10° F. | Sep | Sep | St | St | Sep | St |
| Foam Shake Test (0.2%) | 30 cc | 50 cc | 5 cc | 20 cc | 50 cc | 10 cc |
| After 30 seconds | 0 | 30 cc | 0 | 0 | 20 cc | 0 |
| Foam Pump Test (0.2%) | 2 in | 12 in | 3 in | 2 in | 12 in | 2 in |
| After 30 seconds | | | | | | |

C = Clear
St = Stable

EXAMPLE XII

Another series of concentrate formulae were prepared to prove the merits of ODI. Antimicrobial concentrates containing admixtures of n-octenyl succinic acid and $C_8$–$C_{10}$ monocarboxylic acids were prepared using the solubilizer-coupling agents discussed in Example X. Three formulae were prepared which all had an additional 2 percent Emery 6358 (a 40 percent capric—60 percent caprylic food grade fatty acid blend). The minimum amounts of solubilizer-coupling agent necessary to obtain clear stable concentrate at room temperature. As is demonstrated by this data, significantly less ODI was required to obtain a stable concentrate.

As in Example X, each sample was stored at 120° F., 40° F. and −10° F. Stability at these temperatures again showed the excellent stabilizing power of ODI.

Foam levels were compared using the methods outlined in Example X. The results are shown in Table XIII. As can be seen from these results, ODI causes less foaming than the sulfonate solubilizers.

It is to be appreciated from the preceding that there has been described herein a sanitizer concentrate and use solution which is efficacious in killing off both gram negative and gram positive bacteria as well as yeasts.

Having, thus, described the invention, what is claimed is:

1. An antimicrobial concentrate capable of being diluted to form an antimicrobial use solution, the concentrate comprising:
   (a) an antimicrobial agent selected from the group consisting of a monocarboxylic acid, a dicarboxylic acid and mixtures thereof, the monocarboxylic acid having the general formula:

R‴—COOH wherein R‴ is a straight or branched, saturated or unsaturated alkyl moiety having between about 6 and about 12 carbon atoms, the dicarboxylic acid having the general formula:

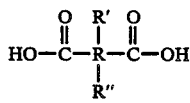

wherein R is a saturated or unsaturated hydrocarbon moiety having 2 carbon atoms; R' is a substituted or unsubstituted n-alkyl or n-alkenyl moiety having about 6 and about 12 carbon atoms; and R″ is a functional group selected from the group consisting of hydrogen and hydroxyl groups;
   (b) an alkyl N,N-dimethyl amine oxide solubilizer-coupling agent having between about 8 and about 10 carbon atoms in the alkyl portion thereof;
   (c) an anionic diluent; and
   (d) an acid capable of yielding a solution pH less than or equal to about 5.0 upon dilution of the concentrate to a use solution.

2. The antimicrobial concentrate of claim 1 which comprises:
   (a) from about 0.25 to about 25.0 percent by weight of the antimicrobial agent, based on the total weight of the concentrate;
   (b) from about 0.25 to about 40 percent by weight of the solubilizer-coupling agent based on the total weight of the concentrate;
   (c) from about 10.0 to about 95.5 percent by weight of the anionic diluent based on the total weight of the concentrate; and
   (d) from about 4.0 to about 50.0 percent by weight of the acid, based on the total weight of the concentrate.

3. The concentrate composition of claim 1 wherein R' in a linear hydrocarbon.

4. The concentrate composition of claim 1 wherein R' has between about 8 and about 10 carbon atoms.

5. The concentrate composition of claim 1 wherein R' is a substituted moiety, the substituent being selected from the group consisting of thiol groups, methane thiol groups, amine groups, methoxy groups, aryl groups and mixtures thereof.

6. The concentrate composition of claim 1 wherein the dicarboxylic acid is selected from the group consisting of n-octyl succinic acid, n-octenyl succinic acid n-nonyl succinic acid, n-nonenyl succinic acid, n-decyl succinic acid, n-decenyl succinic acid, n-hexyl succinic acid, n-hexenyl succinic acid, diisobutenyl succinic acid, methyl heptenyl succinic acid and mixtures thereof.

7. The concentrate composition of claim 1 wherein the antimicrobial agent is selected from the group consisting of succinic acid, maleic acid and fumaric acid and mixtures thereof.

8. The concentrate composition of claim 1 wherein the acid is a weak organic acid selected from the group consisting of acetic acid, hydroxyacetic acid, citric acid, tartaric acid, maleic acid, fumaric acid or mixtures thereof.

9. The concentrate composition of claim 1 wherein the acid is an inorganic acid selected from the group consisting of phosphoric acid, sulfuric acid, sulfamic acid and mixtures thereof.

10. The concentrate composition of claim 1 wherein the acid is a mixture of an inorganic acid and an organic acid, the inorganic acid selected from the group consisting of phosphoric acid, sulfuric acid, sulfamic acid and mixtures thereof, the organic acid selected from the group consisiting of acetic acid, hydroxyacetic acid, citric acid, tartaric acid, maleic acid, fumaric acid and mixtures thereof.

11. The concentrate composition of claim 1 wherein the antimicrobial agent is a monocarboxylic acid selected from the group consisting of capric acid, caprylic acid, octanoic acid, decanoic acid, neodecanoic acid, 2,2 dimethyl octanoic acid and mixtures thereof.

12. The concentrate composition of claim 1 wherein the antimicrobial agent is monocarboxylic acid mixture of mono- and dicarboxylic acid, the monocarboxylic acid being present in a ratio relative to the dicarboxylic acid of between about 1:1 to about 1:20.

13. The concentrate composition of claim 1 wherein the solubilizer-coupling agent is octamamine, N,N, dimethyl-N-oxide.

14. The concentrate composition of claim 1 wherein the diluent is an anionic material selected from the group consisting of short-chain alcohols and water.

15. A low-foaming aqueous, antimicrobial use solution composition comprising:
(a) between about 10 and about 500 ppm of an antimicrobial agent selected from the group consisting of a monocarboxylic acid, a dicarboxylic acid and mixtures thereof, the monocarboxylic acid having the general formula:

R'''—COOH wherein R''' is an alkyl moiety having between about 6 and about 12 carbon atoms, the dicarboxylic acid having the general formula:

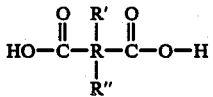

wherein R is a saturated or unsaturated hydrocarbon moiety having 2 carbon atoms; R' is a substituted or unsubstituted n-alkyl or n-alkenyl moiety having about 6 and about 12 carbon atoms; and R'' is a functional group selected from the group consisting of hydrogen and hydroxyl groups;
(b) between about 10 ppm and about 500 ppm of an alkyl N,N-dimethyl amine oxide solubilizer-coupling agent having between about 8 and about 10 carbon atoms in the alkyl portion thereof;
(c) sufficient acid to yield a pH below about 5.0; and
(d) water.

16. The aqueous composition of claim 15 wherein the antimicrobial agent is a dicarboxylic acid selected from the group consisting of n-octyl succinic acid, n-octenyl succinic acid, n-nonyl succinic acid, n-nonenyl succinic acid, n-decyl succinic acid, n-decenyl succinic acid, n-hexyl succinic acid, n-hexenyl succinic acid, diisobutenyl succinic acid, methyl heptenyl succinic acid and mixtures thereof.

17. The aqueous composition of claim 15 wherein the antimicrobial agent is a dicarboxylic acid selected from the group consisting of succinic acid, maleic acid, fumaric acid and mixtures thereof.

18. The aqueous composition of claim 15 wherein the acid is a weak organic acid selected from the group consisting of acetic acid, hydroxyacetic acid, citric acid, tartaric acid, maleic acid, fumaric acid or mixtures thereof.

19. The aqueous composition of claim 15 wherein the acid is an inorganic acid selected from the group consisting of phosphoric acid, sulfuric acid, sulfamic acid and mixtures thereof.

20. The aqueous composition of claim 15 wherein the acid is a mixture of an inorganic acid and an organic acid; the inorganic acid, selected from the group consisting of phosphoric acid, sulfuric acid, sulfamic acid or mixtures thereof, the organic acid selected from the group consisting of acetic acid, hydroxyacetic acid, citric acid, tartaric acid, maleic acid, fumaric acid or mixtures thereof.

* * * * *